United States Patent
Rothgang et al.

(10) Patent No.: US 10,682,199 B2
(45) Date of Patent: Jun. 16, 2020

(54) TRACKING A MARKER IN AN EXAMINATION SUBJECT BY A MAGNETIC RESONANCE TOMOGRAPH

(71) Applicants: Eva Rothgang, Nürnberg (DE); Rainer Schneider, Erlangen (DE)

(72) Inventors: Eva Rothgang, Nürnberg (DE); Rainer Schneider, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 413 days.

(21) Appl. No.: 15/215,312

(22) Filed: Jul. 20, 2016

(65) Prior Publication Data

US 2017/0042632 A1 Feb. 16, 2017

(30) Foreign Application Priority Data

Aug. 13, 2015 (DE) .................. 10 2015 215 476

(51) Int. Cl.
*A61B 90/00* (2016.01)
*A61B 5/055* (2006.01)
(Continued)

(52) U.S. Cl.
CPC .............. *A61B 90/39* (2016.02); *A61B 5/055* (2013.01); *A61B 5/064* (2013.01); *G01R 33/287* (2013.01);
(Continued)

(58) Field of Classification Search
CPC . A61B 90/39; A61B 2090/3954; A61B 34/20; A61B 2034/2055; A61B 2034/2057; A61B 2034/2065; A61B 2034/2072
See application file for complete search history.

(56) References Cited

U.S. PATENT DOCUMENTS 5,034,692 A * 7/1991 Laub .................. G01R 33/5613
                                                    324/309
2003/0098688 A1* 5/2003 Brinker ................ A61B 5/0555
                                                    324/309
(Continued)

FOREIGN PATENT DOCUMENTS

DE      102006023733 A1    12/2007

OTHER PUBLICATIONS

Barbash, Israel M., et al. "Real-time MRI guided percutaneous transthoracic left ventricular access and closure." Journal of Cardiovascular Magnetic Resonance 13.1 (2011): 1.
(Continued)

*Primary Examiner* — Baisakhi Roy
(74) *Attorney, Agent, or Firm* — Lempia Summerfield Katz LLC

(57) ABSTRACT

A magnetic resonance tomograph and a method for tracking a marker in an examination subject by a magnetic resonance tomograph are disclosed. The magnetic resonance tomograph includes a first image recording mode for acquiring the position of the marker. In one act of the method, data for acquiring the position of the marker is recorded with the first image recording mode. In a further act, a position of the marker is determined from the data and a first image with a location-accurate reproduction of the marker is prepared. The recording of the data for acquiring the position of the marker takes place depending on an event.

12 Claims, 2 Drawing Sheets

(51) Int. Cl.
*A61B 5/06* (2006.01)
*G01R 33/28* (2006.01)
(52) U.S. Cl.
CPC ... *A61B 2090/3954* (2016.02); *A61B 2576/00* (2013.01)

(56) References Cited

U.S. PATENT DOCUMENTS

| | | | | |
|---|---|---|---|---|
| 2005/0054913 | A1* | 3/2005 | Duerk | G01R 33/287 600/423 |
| 2005/0148852 | A1* | 7/2005 | Tank | A61B 5/055 600/407 |
| 2005/0245814 | A1 | 11/2005 | Anderson et al. | |
| 2007/0282197 | A1 | 12/2007 | Bill et al. | |
| 2009/0293883 | A1* | 12/2009 | Arn | A61B 90/14 128/845 |
| 2011/0040169 | A1* | 2/2011 | Kamen | A61B 6/037 600/411 |
| 2014/0171784 | A1* | 6/2014 | Ooi | G01R 33/56509 600/414 |
| 2016/0166328 | A1* | 6/2016 | De Vries | A61B 90/30 600/424 |

OTHER PUBLICATIONS

Campbell-Washburn Adrienne E. et. al.: "Spiral imaging for visualization of commercial nitinol guidewires with reduced heating." International Society for Magnetic Resonance in Medicine, 2015, vol. 23, p. 1661.
German Office Action for German Application No. 10 2015 215 476.9, dated May 13, 2016, with English Translation.
Marrouche, Nassir F, et al. "Association of atrial tissue fibrosis identified by delayed enhancement MRI and atrial fibrillation catheter ablation: the DECAAF study." Jama 311.5 (2014): 498-506.
Ricke, Jens, et al. "MR-guided liver tumor ablation employing open high-field 1.0 T MRI for image-guided European brachytherapy." European radiology 20.8 (2010): 1985-1991.
Saikus, Christina E., et al. "MRI-guided vascular access with an active visualization needle." Journal of Magnetic Resonance Imaging 345 (2011): 1159-1166.

* cited by examiner

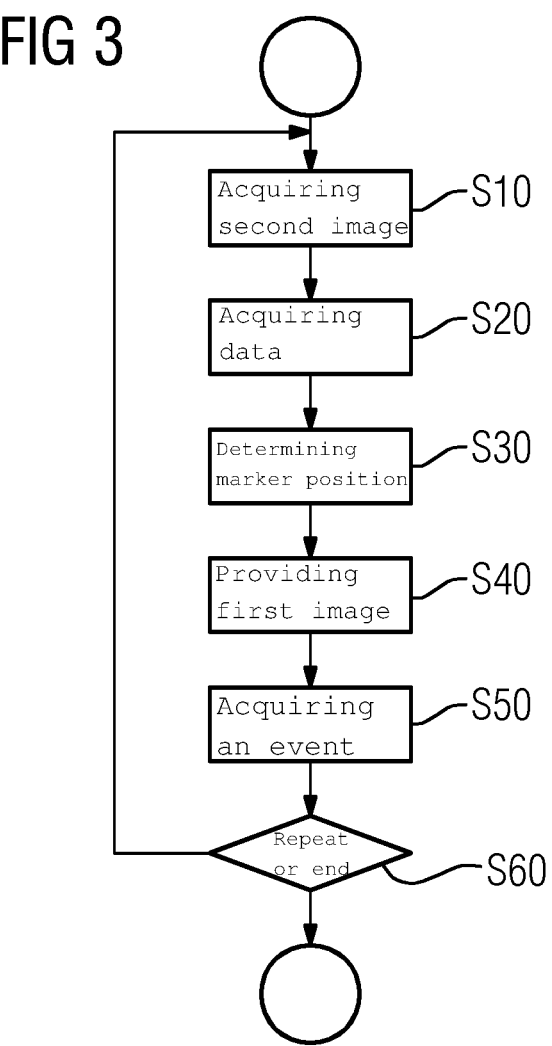

TRACKING A MARKER IN AN EXAMINATION SUBJECT BY A MAGNETIC RESONANCE TOMOGRAPH

This application claims the benefit of DE 10 2015 215 476.9, filed on Aug. 13, 2015, which is hereby incorporated by reference in its entirety.

TECHNICAL FIELD

The embodiments relate to a magnetic resonance tomograph and a method for operating said tomograph for tracking a marker in an examination subject. The magnetic resonance tomograph includes a first image recording mode for acquiring the position of the marker. Data is acquired with the first image recording mode. From the data, a position of the marker is determined and a first image with a location-accurate reproduction of the marker is prepared.

BACKGROUND

Intravascular interventions may be supported by magnetic resonance imaging. This requires that a medical instrument introduced into the body is visualized in order to be able to steer the medical instrument precisely through the body. The automatic detection of the instrument and its visualization or the adaptation of the image planes that are represented to the moving instrument is known as "tracking". Examples of such instruments are catheters or guide wires for catheters.

A distinction is made between active and passive tracking. Passive tracking is based on image artifacts or image properties that are caused by the instrument.

Active tracking requires an apparatus that may receive a position-dependent signal. A signal of this type may be generated by a magnetic resonance pulse sequence or by separate signal generators. The signal may be detected directly.

The detection may take place indirectly via magnetic resonance. Herein, initially atomic nuclei are resonantly excited to the Larmor frequency, which is the frequency at which the spins of the atomic nuclei precess about the direction of the outer magnetic field. The atomic nuclei emit the excitation energy by radiating an electromagnetic wave that also has the Larmor frequency. If this wave has positional information, it may be utilized for active tracking by detection of the wave.

Suitable apparatuses that enable active tracking may be external high frequency antenna units, also referred to below as HF coils, which are able to receive electromagnetic HF signals by induction. Tracking coils of this type may have a small size and may be arranged on a catheter or similar devices. The illumination field of the tracking coil may also be very small, e.g., the spatial interaction region around the external HF coil from which HF signals may be received by the external HF coil.

Tracking information may also be detected in sequences for anatomical imaging. The image acquisition of a magnetic resonance tomograph is a relatively slow modality, in particular as far as high resolution image acquisition is concerned. For precise positioning of a catheter or another device, however, it is precisely a high degree of resolution at the target location that may be needed.

Depending on the tracking type, it is possible to acquire tracking information on the position of the device or the marker with sequences significantly quicker than the sequences for an anatomical image. Such sequences, however, do not provide any, or only too coarse, representations of the anatomy so that no exact position is possible by these sequences.

SUMMARY AND DESCRIPTION

There is a need for a magnetic resonance tomograph and a method that provide better positioning of instruments in an examination subject.

The scope of the present invention is defined solely by the appended claims and is not affected to any degree by the statements within this summary. The present embodiments may obviate one or more of the drawbacks or limitations in the related art.

The method tracks a marker in an examination subject by a magnetic resonance tomograph. The marker may be any device detectable by a magnetic resonance method. For example, active markers in the form of coils or resonance circuits are conceivable, or passive markers in the form, for example, of magnetic materials suitable, through their influence on the fields, to supply information during image acquisition concerning the spatial position of the marker. The position of the marker may be restricted both to the location, and also to information regarding the attitude or orientation of the marker or of an object provided with the marker. The magnetic resonance tomograph includes a first image recording mode for acquiring the position of the marker. The first image recording mode may acquire the data on the position in a shorter time than a subsequently described second image recording mode for anatomical imaging, for example, in half, a fifth, or a tenth of the time for an image acquisition with the second image recording mode. The magnetic resonance tomograph may have a control system for controlling the image acquisition.

In an act of the method, data that includes information relating to the position of the marker is recorded or acquired with the first image recording mode. In a further act of the method, a position of the marker is determined from the data. In another act of the method, a first image is provided with a location-accurate representation of the marker. The expression location-accurate representation may be understood to mean that the position of the marker in relation to the examination subject and/or the magnetic resonance tomograph is to be taken from the first image in one, two, or three dimensions. Herein, the acts of recording the data take place depending on an event. The event may be either a process in the magnetic resonance tomograph or a process relating to the examination subject, the user or the surroundings.

Advantageously, the method is capable of adapting the acquisition of the data to the examination subject so that, for example, an optimum representation of the marker is provided, its position is more precisely shown, and/or the safety of the patient is provided.

The magnetic resonance tomograph and the computer program product share the advantages of the method.

In a possible embodiment, the magnetic resonance tomograph has a second image recording mode for image acquisition of the examination subject. The second image recording mode may provide image data for high-resolution anatomical representations of the examination subject. The method also includes a recording of a second image with the second image recording mode. The data for acquiring the position of the marker and the second image are correlated and merged to a third image. Herein, the third image may be a new image in which elements of the first image and of the second image are combined, the first image is enhanced with elements of the second image or vice versa, the second image is enhanced with a location-accurate representation of the marker.

The third image therefore has image elements of the examination subject from the second image in which or in relation to which the marker is reproduced in a location-accurate manner. The recording or capturing of the second image and/or of the data for acquiring the position of the marker takes place depending on the event. It is equivalent if elements of the first image are adopted into the second image and prepared or if a new third image is prepared with combined elements of the first and second images.

Advantageously, the method is capable of combining the advantages of two image recording modes and therein adapting them to the imaging process and/or the examination subject so that, for example, an optimum representation of the marker is provided, its position being more precisely shown.

In a possible embodiment of the method, the dependency of the recording is a repetition rate for the recording or acquisition of the data.

In an advantageous manner, the repetition rate of the recording of the data for acquiring the position of the marker depending on the event is changed so that, as described below, for example, as a reaction to an operating procedure, the position of the marker is updated in smaller separations in the image so that an instrument or device provided with the marker may be positioned more precisely and quickly.

In a conceivable embodiment of the method, the control system determines the repetition rate depending on the pre-determined limit values.

In magnetic resonance tomographs, legal limit values exist for the specific absorption rate (SAR), and other limit values relating to gradient fields are under discussion. The method and the magnetic resonance tomograph are advantageously capable by the control system of adjusting, for example, the scanning rate so that it does not exceed the limit values.

In a possible embodiment of the method, the magnetic resonance tomograph includes an operating device and the control input is in signal connection with the operating device. The control system executes the recording of the second image and/or the data for acquiring the position of the marker depending on a signal of the operating device.

In this way, the user of the magnetic resonance tomograph may, for example, increase the recording rate of the data in order to be able to position an instrument with the marker more quickly.

In a conceivable embodiment of the method, the magnetic resonance tomograph includes a monitoring device for physiological changes of the examination subject. The control input is in signal connection with the monitoring device so that the control system may carry out the recording of the first image and/or the second image depending on a signal of the monitoring device.

It is therefore advantageously possible, for example, to increase the recording rate for data for acquiring the position of the marker in order, during a movement of the examination subject, to update the representation of the examination subject more rapidly.

In a possible embodiment of the method, the signal input is in signal connection with the position determining unit. The position determining unit generates a signal at the signal input when the marker assumes a pre-determined position. The control system executes the recording of the data for acquiring the position of the marker and/or of the second image depending on a signal of the position determining unit.

It is thus possible, for example, that the magnetic resonance tomograph or the control system thereof increases the repetition rate for the recording of the data for acquiring the position of the marker when the marker approaches a pre-determined intervention region, so that positioning may take place faster and more precisely. Conversely, it is also conceivable that the control system suppresses the recording of the data for acquiring the position of the marker for as long as the marker is situated outside the examination subject, and so reduces the SAR.

The computer program product and the magnetic resonance tomograph share the advantages of the method.

BRIEF DESCRIPTION OF THE DRAWINGS

The above-described properties, features and advantages and the manner in which these are achieved will now be described more clearly and explicitly in conjunction with the following description of the exemplary embodiments, and by reference to the drawings, in which:

FIG. 3 depicts an exemplary schematic flow diagram of a method.

DETAILED DESCRIPTION

Figure 1:
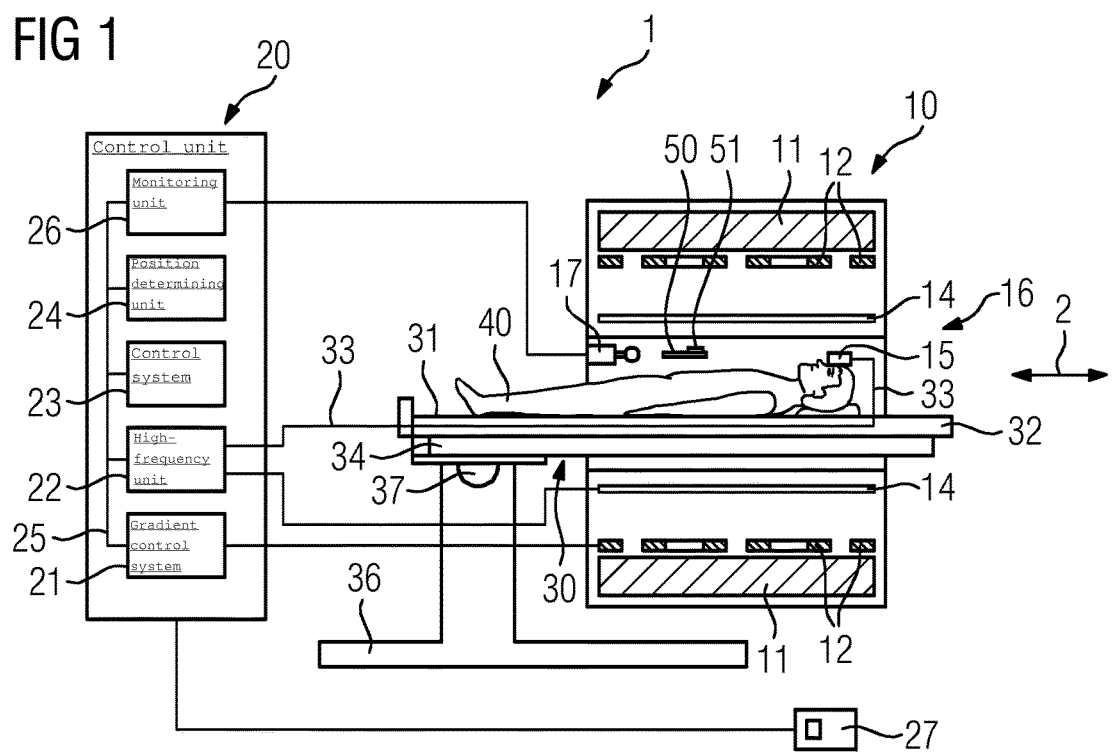
FIG. 1 depicts an exemplary schematic representation of a magnetic resonance tomograph.

FIG. 1 depicts a schematic representation of a magnetic resonance tomograph 1.

The magnet unit 10 has a field magnet 11 that generates a static magnetic field $B_0$ for orienting the nuclear spins of the examination subject or the patient 40 in an examination volume. The examination volume is arranged in a tunnel 16 extending in a longitudinal direction 2 through the magnet unit 10. The field magnet 11 may be a superconducting magnet that may provide magnetic fields with a magnetic flux density of up to 3T and, in some devices, even greater than this. For lower field strengths, however, permanent magnets or electromagnets with normal conducting coils may be used.

Furthermore, the magnet unit 10 has gradient coils 12 configured, for spatial differentiation of the acquired imaging regions in the examination volume, to overlay the magnetic field $B_0$ with variable magnetic fields in three spatial directions. The gradient coils 12 may be coils made of normally conductive wires able to generate fields orthogonal to one another in the examination volume.

The magnet unit 10 also includes a body coil 14 configured to emit a high frequency signal fed via a signal line into the examination volume and to receive resonance signals emitted by the patient 40 and to output them via the signal line. For the emission of the high frequency signal and/or the receiving, the body coil 14 may be replaced by local coils 15 arranged close to the patient 40 in the tunnel 16. It is also conceivable that the local coil 15 is configured for transmitting and receiving and therefore a body coil 14 may be dispensed with.

A control unit 20 supplies the magnet unit 10 with the different signals for the gradient coils 12 and the body coil 14 or the local coils 15 and evaluates the signals received.

Thus, the control unit 20 includes a gradient control system 21 configured to supply the gradient coils 12 via supply lines with variable currents that provide the desired gradient fields in the examination volume temporally coordinated.

Furthermore, the control unit 20 includes a high frequency unit 22 configured to generate a high frequency pulse with a pre-determined temporal sequence, amplitude and spectral power distribution for exciting a magnetic resonance of the nuclear spin in the patient 40. Herein, pulse power levels in the region of kilowatts may be achieved.

The high frequency unit 22 is also configured to evaluate high frequency signals received by the body coil 14 or a local coil 15 and fed via a signal line 33 of the high frequency unit 22 regarding amplitude and phase. This concerns, in particular, high frequency signals which nuclear spins in the patient 40 emit as the response to the excitation by a high frequency pulse in the magnetic field $B_0$ or in a resulting magnetic field from an overlaying of $B_0$ and gradient fields.

Furthermore, the control unit 20 includes a control system 23 configured to undertake the temporal coordination of the activities of the gradient control system 21 and the high frequency unit 22. For this purpose, the control system 23 is connected and in signal exchange via a signal bus 25 with the other units 21, 22. The control system 23 is configured to receive from the high frequency unit 22 evaluated signals from the patient 40 and to process them or to provide and to coordinate pulse and signal forms to the gradient control system 21 and the high frequency unit 22. The gradient control system 21 generates control signals for the gradient coils 12.

A position determining unit 24 of the control unit 20 is configured to determine, from the data acquired in the first image recording mode, the one position of the marker 51.

The marker 51 serves to make visible an instrument 50 for image acquisition in a magnetic resonance tomograph 1. Materials such as metals (e.g., if non-magnetic) may not be detectable in a magnetic resonance tomograph for detecting hydrogen nuclei. Either the markers are visible since materials are used or attached that influence the static magnetic field, the gradient fields or the excitation fields such that the marker 51 is made visible by the image artifacts generated thereby. Or it is possible to provide as markers 51 elements that actively transmit at the Larmor frequency or at least change the excitation locally so that the surroundings appear lighter or darker. This is possible, for example, by resonance elements in the form of resonant circuits with small coils that locally increase the excitation field strength.

The position of the marker 51 may be determined by the position determining unit 24 from data acquired with the first image recording mode by edge detection algorithms (e.g., the Sobel operator) or object recognition algorithms. In this way, not only the location, but also an orientation of the marker 51 or the instrument 50 marked therewith may be determined.

In one conceivable embodiment, the control system 23 is in a signal connection to an operating element 27. In a possible embodiment, the control unit 20 includes a monitoring unit 26 that monitors the patient 40, for example, by sensors 17 or a camera as to whether the patient moves or whether a physiological process or reaction takes place. In this way, the control system 23 is able to detect external events such as, for example, an operating procedure or a heartbeat. The control system 23 may also recognize events by evaluating the data for acquiring the position of the marker 51 and/or of the second image, for example, whether the marker 51 is situated in a pre-determined region of the patient 40 or the examination subject.

The control system is herein configured or programmed or programmable by the computer program product such that, on occurrence of a pre-determined event, the control system 23 carries out the recording of the data for acquiring the position of the marker 51 and/or of the second image depending on the event. It is thus, for example, conceivable that the control system 23 increases the repetition frequency for recordings of the second image in order to enable a more exact anatomical representation for the positioning. It is also conceivable that the repetition frequency for recordings of the data for acquiring the position of the marker is increased in order to follow relatively rapid movements of the marker 51. Also conceivable is a change of the resolution of the first and/or second image recording modes.

In one embodiment, the control system 23 observes pre-determined limit values, for example, for SAR. By way of example, a repetition rate for the first and/or second image recording mode may be reduced if, for example, an estimated or calculated SAR loading exceeds a limit value.

The patient 40 is arranged on a patient table 30. These patient tables 30 are already known from magnetic resonance tomography. The patient table 30 includes a first support 36 arranged under a first end 31 of the patient table 30, opposite from a second end 32 of the patient table 30. So that the support 36 may hold the patient table 30 in a horizontal position, it may have a foot that extends along the patient table 30. In order to move the patient table 30, the foot may also include a movement device, such as rollers. Apart from the support 36, no constructional element is arranged between the floor and the patient table at the first end 31, so that the patient table may be introduced up to the first end 31 into the tunnel 16 of the field magnet 11. In FIG. 1, linear rail systems 34 are depicted that connect the support 36 to the patient table 30 movably so that the patient table may be moved along the longitudinal direction 2. For this purpose, the linear rail system has a drive 37 that enables the patient table 30 to be moved in the longitudinal direction 2 by an operating person or controlled by the control system 23, so that it is also possible to investigate regions of the body of the patient that have a greater extent than the examination volume in the tunnel 16.

Figure 2:
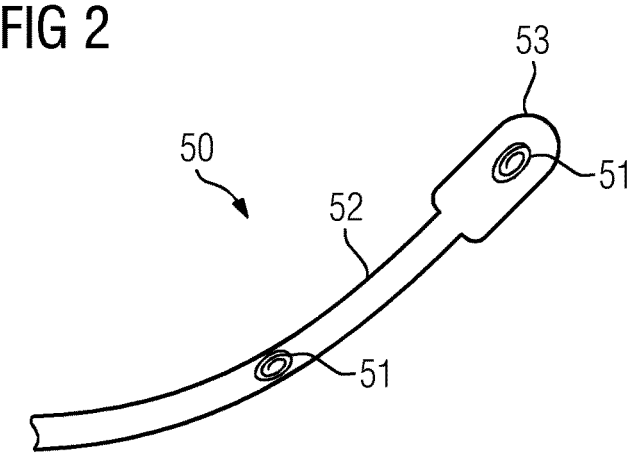
FIG. 2 depicts an exemplary schematic representation of an instrument with a marker.

FIG. 2 depicts, as a possible embodiment of an instrument 50, a schematic representation of a catheter 52. Provided on the catheter 52 at the distal end is a head 53 that includes, for example, a balloon for expanding vessels or for applying a stent. Also conceivable, are other devices such as, for example, electrodes for the ablation of tissue. For tracking the position of the head 53, a marker 51 indicated as a flat coil is arranged thereon. It is also conceivable that the head 53 itself is made, or includes partially, of a material that influences an imaging in the vicinity (e.g., paramagnetic or diamagnetic materials) or itself generates a magnetic resonance signal.

Further markers 51 may be arranged along the catheter 52 in order to render its course or extent in the examination subject.

FIG. 3 depicts a schematic flow diagram of an embodiment of the method.

In act S10, a second image is acquired with a second image recording mode. The second image recording mode provides an anatomical rendering of the examination subject, e.g., details are rendered in high resolution and either two-dimensionally or three-dimensionally. Examples of image acquisition modes of this type are gradient echo sequences or spin echo sequences. The acquired image data is stored by the control system 23 in a memory store. The second image recording mode may also be capable of detecting the marker 51.

It is also conceivable that act S10 is omitted in another possible embodiment of the method, for example, because the position of the examination subject is pre-determined or has been acquired with another method and therefore sufficient information is already available in order to display the examination subject in a second image. It is also conceivable that act S10 is carried out only after the subsequently described act S20.

In act S20 of the method, data is acquired for acquiring the position of the marker 51 with a first image recording mode. The first image recording mode may be configured to detect one or more markers 51 rapidly. In order to accelerate the image acquisition relative to the second image acquisition mode, it is conceivable, for example, that the resolution of the sequence is reduced relative to the second image acquisition mode, the image acquisition is restricted to two-dimensional or one-dimensional imaging or due to the clear signals of the markers 51, a more rapid mode with a smaller signal-to-noise ratio is used. The expression navigator sequences refer to rapid sequences with reduced information content. The acquired image data of the second image may be stored by the control system 23 in a memory store.

In another act S30, a position of the marker 51 is determined in the data acquired in act S20. Various algorithms, (e.g., the Hough transformation), exist for recognizing the contours and thus also the position of the marker 51 in the data. In that the position determining unit 24 uses an algorithm of this type on the stored data, the position of the instrument, and, depending on the type of marker 51 and the instrument 50, also the position of the marker may be determined from the data.

In a further act S40 of the method, a first image is provided in which, on the basis of the data acquired with the first image recording mode, the marker 51 is depicted in a location-accurate manner, e.g., in a position determined in relation to the examination subject.

In a possible embodiment of the method, for this purpose, the data for acquiring the position of the marker 51 and the second image from an image correlation unit is combined and is prepared for reproduction. The image correlation unit may be realized in the control system 23 that has already acquired the data on the position and the second image. For this purpose, in the anatomical or detailed recording of the second image, a reproduction of the marker 51 is superimposed location-accurately with the position determined from the data or an image is stored with a suitable combination from the control system 23 as the first image, so that the marker 51 appears in the anatomical representation at the correct position and in the correct orientation. It is also conceivable to adopt the representation of the marker 51 into the second image or to provide a new third image with the marker 51 of the first image and anatomical elements of the second image. For this purpose, the orientation of the second image and the data for acquiring the position of the marker 51 are also correlated with one another, provided the position data of the marker 51 and the second image have not already been stored with corresponding coordinates following the acquisition.

In a further act S50, the control system 23 acquires an event, for example, by the operating element 27, the monitoring unit 26 or by evaluating the stored first image, the second image and/or the data for acquiring the position of the marker. It is also conceivable that the act S50 is carried out before act S10 or after act S40.

On occurrence of a pre-determined event, the control system 23 carries out the recording of the data for acquiring the position of the marker 51 and/or of the second image depending on the event. It is thus, for example, conceivable that the control system 23 increases the repetition frequency for recordings of the second image in order to enable a more exact anatomical representation for the positioning. It is also conceivable that the repetition frequency for recordings of the data for acquiring the position of the marker 51 is increased in order to follow relatively rapid movements of the marker 51. It is also possible that a data acquisition with the first image acquisition mode takes place only when the marker 51 penetrates into the examination subject or is detected in its immediate vicinity in the second image recording mode. Also conceivable is a change of the resolution of the first and/or second image recording modes or other adaptations to the situation. In an embodiment, the control system 23 takes account of pre-determined limit values so that, for example, limit values for SAR are not exceeded.

Predetermined events may be, for example, an actuation of the operating element 27 by an operator. The operating element may herein be a simple foot switch or equally a graphical user interface or a speech recognition unit or a gesture recognition unit. Conceivable events may also be movements detected by the monitoring unit 26 or physiological actions or reactions of the examination subject. Finally, it may also be an event if the control system 23 detects a process by evaluating the first and/or second image, for example, if the marker 51 is situated in a pre-defined volume, enters or leaves it, or overshoots or undershoots a pre-determined movement speed or the like.

The method may continue after act S60 with act S10, wherein depending on the event, on repetition of acts S10 and S20, these may be carried out by the control system 23 modified. It is also conceivable that in some repetition loops, act S10 or S20 is omitted respectively, in order to enable a higher repetition rate for the remaining image acquisition act.

Once the examination is complete, the method may be ended, for example, by an event such as a user operation, time expiry, removing the marker from the examination region or similar processes.

In principle, the subunits of the control unit 20 may be configured as separate hardware units, but also as software modules on a single processor platform of the control unit 20.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for tracking a marker in an examination subject by a magnetic resonance tomograph, wherein the magnetic resonance tomograph comprises a first image recording mode for acquiring a position of the marker and a second image recording mode for image acquisition of the examination subject, wherein the method comprises:
   recording an image of the examination subject with the second image recording mode of the magnetic resonance tomograph;
   iteratively recording data, by the magnetic resonance tomograph, to acquire the position of the marker with the first image recording mode, wherein the first image recording mode has a reduced image resolution relative to the second image recording mode, therein providing an accelerated image acquisition for acquiring the position of the marker;
   determining, by the magnetic resonance tomograph, the position of the marker from the data; and
   producing, by the magnetic resonance tomograph, a first image with a location-accurate reproduction of the marker based on the determined position,
   wherein a repetition rate for the recording of the data for acquiring the position of the marker with the first image recording mode is increased when the marker assumes a pre-determined position or approaches a pre-determined intervention region within the examination subject so that an instrument or device provided with the marker is configured to be positioned more precisely and more quickly within the examination subject.

2. The method of claim 1, further comprising:
   correlating the image of the examination subject with the first image; and
   producing an additional image with an image element of the examination subject from the image of the examination subject and the location-accurate reproduction of the marker,
   wherein the recording of the image of the examination subject takes place depending on an event.

3. The method of claim 2, wherein the event is an operating procedure by a user.

4. The method of claim 2, wherein the event is a physiological reaction of the examination subject.

5. The method of claim 1, wherein the repetition rate is determined depending on pre-determined limit values.

6. A magnetic resonance tomograph device comprising:
   a computer; and
   a computer program comprising machine code stored on a data carrier of the computer,
   wherein the machine code of the computer program is configured to be executed by the computer, and the execution of which causes the magnetic resonance tomograph device to:
      record an image of an examination subject with a second image recording mode;
      iteratively record data to acquire a position of a marker with a first image recording mode, wherein the first image recording mode is restricted to a two-dimensional or a one-dimensional imaging mode to provide an accelerated image acquisition mode relative to the second image recording mode;
      determine the position of the marker from the data; and
      produce a first image with a location-accurate reproduction of the marker based on the determined position,
      wherein a repetition rate for the recording of the data for the acquiring of the position of the marker is increased when the marker assumes a pre-determined position or approaches a pre-determined intervention region within the examination subject so that an instrument or device provided with the marker is configured to be positioned more precisely and more quickly within the examination subject.

7. A magnetic resonance tomograph for tracking a marker in an examination subject, the magnetic resonance tomograph comprising:
   a first image recording mode for acquiring a position of the marker;
   a second image recording mode for image acquisition of the examination subject; and
   a control system for controlling the image acquisition and recording of data for the acquiring of the position of the marker,
   wherein the magnetic resonance tomograph is configured to:
      record an image of the examination subject with the second image recording mode,
      iteratively record the data for acquiring the position of the marker with the first image recording mode, wherein the first image recording mode is an accelerated image recording mode having a smaller signal-to-noise ratio relative to the second image recording mode,
      determine the position of the marker from the data, and
      generate a first image with a location-accurate reproduction of the marker based on the determined position,
      wherein a repetition rate for the recording of the data for the acquiring of the position of the marker is increased when the marker assumes a pre-determined position or approaches a pre-determined intervention region within the examination subject so that an instrument or device provided with the marker is configured to be positioned more precisely and more quickly within the examination subject.

8. The magnetic resonance tomograph of claim 7, wherein the magnetic resonance tomograph is configured to correlate the image of the examination subject with the first image and to produce an additional image with an image element of the examination subject from the image of the examination subject and the location-accurate reproduction of the marker.

9. The magnetic resonance tomograph of claim 8, further comprising:
   an operating device,
   wherein the control system is configured to record the image of the examination subject and/or the data for acquiring the position of the marker depending on a signal of the operating device.

10. The magnetic resonance tomograph of claim 7, wherein the control system is configured to determine the repetition rate depending on pre-determined limit values.

11. The magnetic resonance tomograph of claim 7, further comprising:
   a sensor or camera configured to monitor physiological changes of the examination subject,
   wherein the control system is configured to record the first image and/or the data depending on a signal of the sensor or camera.

12. The magnetic resonance tomograph of claim 7, wherein the magnetic resonance tomograph is configured to generate a signal when the marker assumes the pre-determined position.

* * * * *